United States Patent
Kang et al.

(10) Patent No.: US 12,048,760 B2
(45) Date of Patent: Jul. 30, 2024

(54) LONG LASTING COSMETIC COMPOSITIONS

(71) Applicant: Living Proof, Inc., Boston, MA (US)

(72) Inventors: Soo-Young Kang, Newton, MA (US);
Zhaoxia Ji, Natick, MA (US);
Ling-Fang Tseng, Boston, MA (US);
Dinara A. Villanueva, Boston, MA (US)

(73) Assignee: Living Proof, Inc., Boston, MA (US)

( * ) Notice: Subject to any disclaimer, the term of this patent is extended or adjusted under 35 U.S.C. 154(b) by 827 days.

(21) Appl. No.: 17/050,803

(22) PCT Filed: Apr. 26, 2019

(86) PCT No.: PCT/US2019/029274
§ 371 (c)(1),
(2) Date: Oct. 26, 2020

(87) PCT Pub. No.: WO2019/210121
PCT Pub. Date: Oct. 31, 2019

(65) Prior Publication Data
US 2021/0212920 A1    Jul. 15, 2021

(51) Int. Cl.
| | |
|---|---|
| *A61K 8/87* | (2006.01) |
| *A61Q 5/06* | (2006.01) |
| *C08G 18/08* | (2006.01) |
| *C08G 18/32* | (2006.01) |
| *C08G 18/38* | (2006.01) |
| *C08G 18/44* | (2006.01) |
| *C08G 18/66* | (2006.01) |
| *C08G 18/75* | (2006.01) |

(52) U.S. Cl.
CPC ............ *A61K 8/87* (2013.01); *A61Q 5/06* (2013.01); *C08G 18/0823* (2013.01); *C08G 18/3206* (2013.01); *C08G 18/3821* (2013.01); *C08G 18/44* (2013.01); *C08G 18/6644* (2013.01); *C08G 18/6648* (2013.01); *C08G 18/755* (2013.01)

(58) Field of Classification Search
CPC ........ A61K 8/87; A61Q 5/06; C08G 18/0823; C08G 18/3206; C08G 18/3821; C08G 18/44; C08G 18/6644; C08G 18/6648; C08G 18/755
See application file for complete search history.

(56) References Cited

U.S. PATENT DOCUMENTS

| | | |
|---|---|---|
| 3,104,424 A | 9/1963 | Immel |
| 3,262,686 A | 7/1966 | Kraus et al. |
| 3,803,063 A | 4/1974 | Krentz, Jr. |
| 3,973,901 A | 8/1976 | Micchelli et al. |
| 4,071,614 A | 1/1978 | Grimm, III |
| 4,455,146 A | 6/1984 | Noda et al. |
| 4,950,542 A | 8/1990 | Barker |
| 5,110,852 A | 5/1992 | Gogolewski et al. |
| 5,281,654 A | 1/1994 | Eisenhart et al. |
| 5,290,543 A | 3/1994 | Ounanian et al. |
| 5,335,373 A | 8/1994 | Dresdner, Jr. et al. |
| 5,354,807 A | 10/1994 | Dochniak |
| 5,357,636 A | 10/1994 | Dresdner, Jr. et al. |
| 5,362,486 A | 11/1994 | Nandagiri et al. |
| 5,534,265 A | 7/1996 | Fowler et al. |
| 5,534,348 A | 7/1996 | Miller et al. |
| 5,540,853 A | 7/1996 | Trinh et al. |
| 5,626,840 A | 5/1997 | Thomaides et al. |
| 5,637,291 A | 6/1997 | Bara et al. |
| 5,643,581 A | 7/1997 | Mougin et al. |
| 5,720,961 A | 2/1998 | Fowler et al. |
| 5,733,572 A | 3/1998 | Unger et al. |
| 5,807,540 A | 9/1998 | Junino et al. |
| 5,833,967 A | 11/1998 | Ramin |
| 5,846,551 A | 12/1998 | DaCunha et al. |
| 5,849,310 A | 12/1998 | Trinh et al. |
| 5,891,463 A | 4/1999 | Bello et al. |
| 5,900,457 A | 5/1999 | Duan et al. |
| 5,912,299 A | 6/1999 | Tomko et al. |
| 5,914,117 A | 6/1999 | Lavaud |
| 5,932,194 A | 8/1999 | Plessix et al. |
| 5,932,200 A | 8/1999 | Reich et al. |
| 5,993,972 A | 11/1999 | Reich et al. |
| 6,007,793 A | 12/1999 | Bhatt et al. |
| 6,084,051 A | 7/2000 | Blum et al. |
| 6,086,903 A | 7/2000 | Trinh et al. |
| 6,106,813 A | 8/2000 | Mondet et al. |
| 6,126,930 A | 10/2000 | Dubois et al. |
| 6,130,309 A | 10/2000 | Reich et al. |
| 6,132,704 A | 10/2000 | Bhatt et al. |

(Continued)

FOREIGN PATENT DOCUMENTS

| | | |
|---|---|---|
| BR | PI0405064 A | 8/2005 |
| BR | 102013022835 A2 | 8/2015 |

(Continued)

OTHER PUBLICATIONS

U.S. Appl. No. 15/451,897, filed Mar. 7, 2017, 2017-0258700, Published.
U.S. Appl. No. 16/348,644, filed May 9, 2019, 2019-0359786, Abandoned.
U.S. Appl. No. 16/128,620, filed Sep. 12, 2018, U.S. Pat. No. 10,987,300, Issued.
U.S. Appl. No. 17/231,587, filed Apr. 15, 2021, Abandoned.
U.S. Appl. No. 17/530,662, filed Nov. 19, 2021, Pending.
U.S. Appl. No. 16/128,622, filed Sep. 12, 2018, U.S. Pat. No. 10,842,729, Issued.
U.S. Appl. No. 17/071,198, filed Oct. 15, 2020, Abandoned.
U.S. Appl. No. 17/326,605, filed May 21, 2021, 2022-0105021, Published.
U.S. Appl. No. 16/195,584, filed Nov. 19, 2018, 2019-0151221, Published.

(Continued)

*Primary Examiner* — Sean M Basquill
(74) *Attorney, Agent, or Firm* — McCarter & English, LLP; Michael J. DeGrazia

(57) ABSTRACT

Provided are hair treatment compositions comprising a polyurethane-urea crosslinked by at least one multi-functional chain extender, and uses thereof.

15 Claims, 4 Drawing Sheets

(56) References Cited

U.S. PATENT DOCUMENTS

| | | |
|---|---|---|
| 6,153,179 A | 11/2000 | Blankenburg et al. |
| 6,156,325 A | 12/2000 | Farer et al. |
| 6,221,344 B1 | 4/2001 | Ramin et al. |
| 6,238,651 B1 | 5/2001 | Bara |
| 6,254,876 B1 | 7/2001 | de la Poterie et al. |
| 6,277,386 B1 | 8/2001 | Kim et al. |
| 6,277,401 B1 | 8/2001 | Bello et al. |
| 6,291,580 B1 | 9/2001 | Kukkala et al. |
| 6,298,558 B1 | 10/2001 | Tseng et al. |
| 6,319,959 B1 | 11/2001 | Mougin et al. |
| 6,326,013 B1 | 12/2001 | Lemann et al. |
| 6,346,234 B1 | 2/2002 | Rollat et al. |
| 6,361,782 B1 | 3/2002 | Chevalier et al. |
| 6,365,697 B1 | 4/2002 | Kim et al. |
| 6,372,876 B1 | 4/2002 | Kim et al. |
| 6,403,070 B1 | 6/2002 | Pataut et al. |
| 6,403,107 B1 | 6/2002 | Lemann |
| 6,403,542 B1 | 6/2002 | Maurin et al. |
| 6,409,998 B1 | 6/2002 | Candau et al. |
| 6,433,073 B1 | 8/2002 | Kantner et al. |
| 6,465,534 B2 | 10/2002 | Fukuzawa et al. |
| 6,469,227 B1 | 10/2002 | Cooke et al. |
| 6,485,950 B1 | 11/2002 | Kumar et al. |
| 6,517,821 B1 | 2/2003 | Rollat et al. |
| 6,520,186 B2 | 2/2003 | Rollat et al. |
| 6,524,564 B1 | 2/2003 | Kim et al. |
| 6,524,597 B2 | 2/2003 | Kashimoto |
| 6,531,118 B1 | 3/2003 | Gonzalez et al. |
| 6,555,096 B2 | 4/2003 | Carrion et al. |
| 6,576,024 B1 | 6/2003 | Lang et al. |
| 6,576,702 B2 | 6/2003 | Anderle et al. |
| 6,579,517 B1 | 6/2003 | Kim et al. |
| 6,592,881 B1 | 7/2003 | Fukuda et al. |
| 6,613,314 B1 | 9/2003 | Rollat et al. |
| 6,635,262 B2 | 10/2003 | Jourdan et al. |
| 6,641,804 B1 | 11/2003 | Ohta et al. |
| 6,682,748 B1 | 1/2004 | De La Poterie et al. |
| 6,689,345 B2 | 2/2004 | Jager Lezer |
| 6,692,729 B1 | 2/2004 | Asaoka et al. |
| 6,719,959 B1 | 4/2004 | Gonzalez et al. |
| 6,730,289 B2 | 5/2004 | Khoshdel |
| 6,750,291 B2 | 6/2004 | Kim et al. |
| 6,800,276 B2 | 10/2004 | Kim et al. |
| 6,830,758 B2 | 12/2004 | Nichols et al. |
| 6,884,853 B1 | 4/2005 | Asaoka et al. |
| 6,897,281 B2 | 5/2005 | Lubnin et al. |
| 6,927,254 B2 | 8/2005 | Melchiors et al. |
| 7,019,061 B2 | 3/2006 | Meffert et al. |
| 7,098,178 B2 | 8/2006 | Gerke et al. |
| 7,101,954 B2 | 9/2006 | Zofchak et al. |
| 7,160,553 B2 | 1/2007 | Gibbins et al. |
| 7,326,256 B2 | 2/2008 | Cottard et al. |
| 7,348,299 B2 | 3/2008 | Keenan et al. |
| 7,445,770 B2 | 11/2008 | Berezkin et al. |
| 7,452,525 B1 | 11/2008 | Berezkin et al. |
| 7,481,996 B2 | 1/2009 | Ishii et al. |
| 7,659,233 B2 | 2/2010 | Hurley et al. |
| 7,700,082 B2 | 4/2010 | Mallo et al. |
| 7,740,832 B1 | 6/2010 | Rollat-Corvol et al. |
| 7,744,911 B2 | 6/2010 | Pechko et al. |
| RE41,615 E | 8/2010 | Kim et al. |
| 7,829,099 B2 | 11/2010 | Woeller et al. |
| 7,907,346 B2 | 3/2011 | Swarup et al. |
| 7,914,775 B2 | 3/2011 | Cottard et al. |
| 7,959,903 B2 | 6/2011 | Candau et al. |
| 7,972,589 B2 | 7/2011 | Leighton et al. |
| 7,998,465 B2 | 8/2011 | De La Poterie et al. |
| 8,067,355 B2 | 11/2011 | Smets et al. |
| 8,258,093 B2 | 9/2012 | Van Dyke |
| 8,343,523 B2 | 1/2013 | Toreki et al. |
| 8,449,871 B2 | 5/2013 | Mougin et al. |
| 8,497,338 B2 | 7/2013 | Bai et al. |
| 8,623,388 B2 | 1/2014 | Rajaiah et al. |
| 8,629,213 B2 | 1/2014 | Hidalgo et al. |
| 8,679,050 B2 | 3/2014 | Nakamura |
| 8,679,465 B2 | 3/2014 | Malnou et al. |
| 8,685,377 B2 | 4/2014 | Kaftan et al. |
| 8,734,772 B1 | 5/2014 | Zhou et al. |
| 8,741,333 B2 | 6/2014 | Zhang et al. |
| 8,784,854 B2 | 7/2014 | Choi et al. |
| 8,871,817 B2 | 10/2014 | Turk et al. |
| 8,882,902 B2 | 11/2014 | Suzuki et al. |
| 8,895,040 B2 | 11/2014 | Vondruska et al. |
| 8,956,160 B2 | 2/2015 | Willison et al. |
| 8,956,162 B2 | 2/2015 | De Vreese et al. |
| 9,016,221 B2 | 4/2015 | Brennan et al. |
| RE45,538 E | 6/2015 | Smets et al. |
| 9,079,152 B2 | 7/2015 | Markus et al. |
| 9,101,143 B2 | 8/2015 | Markus et al. |
| 9,102,783 B2 | 8/2015 | Yagi et al. |
| 9,175,125 B2 | 11/2015 | Turk et al. |
| 9,295,632 B1 | 3/2016 | Benn et al. |
| 9,340,650 B2 | 5/2016 | Wagner et al. |
| 9,393,218 B2 | 7/2016 | Zurdo Schroeder et al. |
| 9,458,354 B2 * | 10/2016 | Felice ............... C08G 18/0823 |
| 10,842,729 B2 | 11/2020 | Kang et al. |
| 2001/0031280 A1 | 10/2001 | Ferrari et al. |
| 2002/0028875 A1 | 3/2002 | Anderle et al. |
| 2002/0034480 A1 | 3/2002 | Grimm et al. |
| 2002/0034486 A1 | 3/2002 | Midha et al. |
| 2002/0102222 A1 | 8/2002 | Carrion et al. |
| 2002/0107314 A1 | 8/2002 | Pinzon et al. |
| 2002/0114773 A1 | 8/2002 | Kanji et al. |
| 2002/0155962 A1 | 10/2002 | Cincotta et al. |
| 2002/0164297 A1 | 11/2002 | Ferrari et al. |
| 2002/0192273 A1 | 12/2002 | Buseman et al. |
| 2003/0026815 A1 | 2/2003 | Scott et al. |
| 2003/0064086 A1 | 4/2003 | Carrion et al. |
| 2003/0082126 A9 | 5/2003 | Pinzon et al. |
| 2003/0086886 A1 | 5/2003 | Midha |
| 2003/0086896 A1 | 5/2003 | Midha et al. |
| 2003/0099694 A1 | 5/2003 | Cevc et al. |
| 2003/0125427 A9 | 7/2003 | Pinzon et al. |
| 2003/0185780 A1 | 10/2003 | Ferrari et al. |
| 2003/0190345 A1 | 10/2003 | Cordes et al. |
| 2003/0191154 A1 | 10/2003 | Kalafsky et al. |
| 2003/0198659 A1 | 10/2003 | Hoffmann et al. |
| 2003/0203991 A1 | 10/2003 | Schottman et al. |
| 2004/0001798 A1 | 1/2004 | Perron et al. |
| 2004/0057914 A1 | 3/2004 | Bonda et al. |
| 2004/0071757 A1 | 4/2004 | Rolf |
| 2004/0086482 A1 | 5/2004 | Zofchak et al. |
| 2004/0120915 A1 | 6/2004 | Yang et al. |
| 2004/0131573 A1 | 7/2004 | Tang |
| 2004/0137028 A1 | 7/2004 | de la Poterie |
| 2004/0156804 A1 | 8/2004 | Poterie et al. |
| 2004/0166076 A1 | 8/2004 | Ferrari et al. |
| 2004/0166133 A1 | 8/2004 | Cavazzuti et al. |
| 2004/0176487 A1 | 9/2004 | Svedberg et al. |
| 2004/0186259 A1 | 9/2004 | Brehm et al. |
| 2004/0197286 A1 | 10/2004 | Robert et al. |
| 2004/0223987 A1 | 11/2004 | Ferrari |
| 2004/0228886 A1 | 11/2004 | Ding et al. |
| 2004/0247549 A1 | 12/2004 | Lu et al. |
| 2005/0008667 A1 | 1/2005 | Liechty et al. |
| 2005/0014674 A1 | 1/2005 | Liechty et al. |
| 2005/0043209 A1 | 2/2005 | Schmiedel et al. |
| 2005/0089540 A1 | 4/2005 | Uchiyama et al. |
| 2005/0118126 A1 | 6/2005 | Rollat et al. |
| 2005/0148753 A1 | 7/2005 | Nguyen-Kim et al. |
| 2005/0163741 A1 | 7/2005 | Zech |
| 2005/0169873 A1 | 8/2005 | Rollat et al. |
| 2005/0169874 A1 | 8/2005 | Zofchak et al. |
| 2005/0209428 A1 | 9/2005 | Tamareselvy |
| 2005/0220740 A1 | 10/2005 | Dumousseaux |
| 2005/0220741 A1 | 10/2005 | Dumousseaux |
| 2005/0249691 A1 | 11/2005 | Monks et al. |
| 2005/0257330 A1 | 11/2005 | Noecker et al. |
| 2005/0276831 A1 | 12/2005 | Dihora et al. |
| 2005/0287100 A1 | 12/2005 | Lebre |
| 2005/0287103 A1 | 12/2005 | Filippi et al. |
| 2005/0287182 A1 | 12/2005 | Monks et al. |
| 2005/0287183 A1 | 12/2005 | Lebre |
| 2006/0045890 A1 | 3/2006 | Gonzalez et al. |

(56) References Cited

U.S. PATENT DOCUMENTS

| | | |
|---|---|---|
| 2006/0045893 A1 | 3/2006 | Yu et al. |
| 2006/0051311 A1 | 3/2006 | Walter et al. |
| 2006/0073106 A1 | 4/2006 | Berg-Schultz et al. |
| 2006/0078519 A1 | 4/2006 | Lion et al. |
| 2006/0083762 A1 | 4/2006 | Brun et al. |
| 2006/0099550 A1 | 5/2006 | Faasse et al. |
| 2006/0120983 A1 | 6/2006 | Blin et al. |
| 2006/0134049 A1 | 6/2006 | Keenan et al. |
| 2006/0171984 A1 | 8/2006 | Cromack et al. |
| 2006/0193789 A1 | 8/2006 | Tamarkin et al. |
| 2006/0216250 A1 | 9/2006 | Schultz et al. |
| 2006/0233728 A1 | 10/2006 | Sagawa et al. |
| 2006/0281650 A1 | 12/2006 | Keenan et al. |
| 2006/0287219 A1 | 12/2006 | Dykstra et al. |
| 2007/0032605 A1 | 2/2007 | Harashina |
| 2007/0105977 A1 | 5/2007 | Gabriel et al. |
| 2007/0167565 A1 | 7/2007 | Rische et al. |
| 2007/0183992 A1 | 8/2007 | Dumousseaux et al. |
| 2007/0183997 A9 | 8/2007 | Lebre et al. |
| 2007/0189980 A1 | 8/2007 | Zhang et al. |
| 2007/0197704 A1 | 8/2007 | Walter et al. |
| 2007/0207222 A1 | 9/2007 | Yu et al. |
| 2007/0251026 A1 | 11/2007 | Lalleman et al. |
| 2008/0044373 A1 | 2/2008 | Tekti et al. |
| 2008/0044445 A1 | 2/2008 | Rubin |
| 2008/0045985 A1 | 2/2008 | Gurtner et al. |
| 2008/0138368 A1 | 6/2008 | Lezer |
| 2008/0175875 A1 | 7/2008 | Sunkara |
| 2008/0254074 A1 | 10/2008 | Dussaud et al. |
| 2009/0041683 A1 | 2/2009 | Molenda et al. |
| 2009/0049623 A1 | 2/2009 | Brown et al. |
| 2009/0056734 A1 | 3/2009 | Bacon |
| 2009/0061004 A1 | 3/2009 | Birkel et al. |
| 2009/0105195 A1 | 4/2009 | O'Brien |
| 2009/0112141 A1 | 4/2009 | Derr |
| 2009/0175928 A1 | 7/2009 | Maier et al. |
| 2009/0196842 A1 | 8/2009 | Zech et al. |
| 2009/0257960 A1 | 10/2009 | Kim et al. |
| 2009/0263338 A1 | 10/2009 | Rolland et al. |
| 2009/0285866 A1 | 11/2009 | Afriat et al. |
| 2010/0003198 A1 | 1/2010 | Stolmeier et al. |
| 2010/0233146 A1 | 9/2010 | McDaniel |
| 2010/0260687 A1 | 10/2010 | Yu et al. |
| 2010/0261629 A1 | 10/2010 | Smets et al. |
| 2010/0297036 A1 | 11/2010 | Feuillette |
| 2010/0325812 A1 | 12/2010 | Panandiker et al. |
| 2010/0325813 A1 | 12/2010 | Dykstra et al. |
| 2011/0010817 A1 | 1/2011 | Theberge et al. |
| 2011/0027211 A1 | 2/2011 | Viala et al. |
| 2011/0046286 A1* | 2/2011 | Lubnin .............. B82Y 30/00 977/773 |
| 2011/0067720 A1 | 3/2011 | Ranade et al. |
| 2011/0117042 A1 | 5/2011 | Viala et al. |
| 2011/0200927 A1 | 8/2011 | Jung et al. |
| 2011/0229430 A1 | 9/2011 | Hawkins et al. |
| 2011/0230474 A1 | 9/2011 | Grigorian et al. |
| 2011/0256311 A1 | 10/2011 | Mattos, Jr. |
| 2011/0272320 A1 | 11/2011 | Alwattari et al. |
| 2011/0274633 A1 | 11/2011 | Vu et al. |
| 2012/0207696 A1 | 8/2012 | van Geel et al. |
| 2012/0255574 A1 | 10/2012 | Flohr et al. |
| 2013/0084256 A1 | 4/2013 | Li et al. |
| 2013/0161349 A1 | 6/2013 | Pfeiffenberger |
| 2013/0196849 A1 | 8/2013 | Combs et al. |
| 2013/0239344 A1 | 9/2013 | Stolarz, Jr. et al. |
| 2013/0239874 A1 | 9/2013 | Smith et al. |
| 2013/0261255 A1 | 10/2013 | Deyrail et al. |
| 2013/0344019 A1 | 12/2013 | Weber et al. |
| 2014/0010776 A1 | 1/2014 | Viala et al. |
| 2014/0044657 A1 | 2/2014 | Kelly et al. |
| 2014/0066496 A1 | 3/2014 | Gunari et al. |
| 2014/0086864 A1 | 3/2014 | Ishimori et al. |
| 2014/0105846 A1 | 4/2014 | Viala et al. |
| 2014/0142191 A1 | 5/2014 | De La Zerda et al. |
| 2014/0147396 A1 | 5/2014 | Sertchook et al. |
| 2014/0170327 A1 | 6/2014 | Dombrowski et al. |
| 2014/0219927 A1 | 8/2014 | Belluscio et al. |
| 2014/0248270 A1 | 9/2014 | Yu et al. |
| 2014/0248340 A1 | 9/2014 | Schwarzentruber et al. |
| 2014/0350269 A1 | 11/2014 | Eiji Borges Sato |
| 2015/0004117 A1 | 1/2015 | Tan et al. |
| 2015/0004200 A1 | 1/2015 | Brown et al. |
| 2015/0007849 A1 | 1/2015 | Cajan et al. |
| 2015/0071978 A1 | 3/2015 | Chang |
| 2015/0118331 A1 | 4/2015 | Boam et al. |
| 2015/0119497 A1 | 4/2015 | Matsui et al. |
| 2015/0190450 A1 | 7/2015 | Chang |
| 2015/0238406 A1 | 8/2015 | Pohlmann et al. |
| 2015/0283041 A1 | 10/2015 | Benn et al. |
| 2015/0342845 A1 | 12/2015 | Hwang et al. |
| 2015/0344622 A1 | 12/2015 | Mukerjee et al. |
| 2016/0001099 A1 | 1/2016 | Castro et al. |
| 2016/0058678 A1 | 3/2016 | Smets et al. |
| 2016/0074311 A1 | 3/2016 | Massey-Brooker et al. |
| 2016/0143836 A1 | 5/2016 | Hayes et al. |
| 2016/0175233 A1 | 6/2016 | Benn |
| 2016/0175238 A1 | 6/2016 | Shin et al. |
| 2016/0184195 A1 | 6/2016 | Tan et al. |
| 2016/0220475 A1 | 8/2016 | Scherner et al. |
| 2017/0216188 A1 | 8/2017 | Bermudez Agudelo et al. |
| 2017/0258700 A1 | 9/2017 | Kang et al. |
| 2018/0000699 A1 | 1/2018 | Trahan |
| 2019/0076347 A1 | 3/2019 | Kang et al. |
| 2019/0151221 A1 | 5/2019 | Kang et al. |
| 2019/0359786 A1 | 11/2019 | Trahan et al. |
| 2022/0105021 A1 | 4/2022 | Kang et al. |

FOREIGN PATENT DOCUMENTS

| | | |
|---|---|---|
| CN | 1236783 A | 12/1999 |
| CN | 1370063 A | 9/2002 |
| CN | 1370185 A | 9/2002 |
| CN | 1413102 A | 4/2003 |
| CN | 1476320 A | 2/2004 |
| CN | 1487962 A | 4/2004 |
| CN | 1607934 A | 4/2005 |
| CN | 1650840 A | 8/2005 |
| CN | 1708524 A | 12/2005 |
| CN | 1775826 A | 5/2006 |
| CN | 101124256 A | 2/2008 |
| CN | 101130082 A | 2/2008 |
| CN | 101361701 A | 2/2009 |
| CN | 101484130 A | 7/2009 |
| CN | 101980691 A | 2/2011 |
| CN | 102015803 A | 4/2011 |
| CN | 102575051 A | 7/2012 |
| CN | 102895164 A | 1/2013 |
| CN | 103314025 A | 9/2013 |
| CN | 103705401 A | 4/2014 |
| CN | 104188877 A | 12/2014 |
| CN | 105213260 A | 1/2016 |
| CN | 105561841 A | 5/2016 |
| CN | 105764484 A | 7/2016 |
| CN | 109071750 A | 12/2018 |
| DE | 102015204154 A1 | 9/2016 |
| EP | 727981 A1 | 8/1996 |
| EP | 746377 A1 | 12/1996 |
| EP | 789550 A1 | 8/1997 |
| EP | 923927 A1 | 6/1999 |
| EP | 1058560 A1 | 12/2000 |
| EP | 1082953 A1 | 3/2001 |
| EP | 1090632 A1 | 4/2001 |
| EP | 1090633 A1 | 4/2001 |
| EP | 1092419 A1 | 4/2001 |
| EP | 1155676 A2 | 11/2001 |
| EP | 1161937 A2 | 12/2001 |
| EP | 1216690 A2 | 6/2002 |
| EP | 1218430 A1 | 7/2002 |
| EP | 1289363 A1 | 3/2003 |
| EP | 1417886 A1 | 5/2004 |
| EP | 1419759 A2 | 5/2004 |
| EP | 1440680 A1 | 7/2004 |
| EP | 1481661 A2 | 12/2004 |
| EP | 1491179 A2 | 12/2004 |

(56) References Cited

FOREIGN PATENT DOCUMENTS

| | | |
|---|---|---|
| EP | 1579841 A1 | 9/2005 |
| EP | 1579849 A1 | 9/2005 |
| EP | 1598046 A1 | 11/2005 |
| EP | 1604634 A1 | 12/2005 |
| EP | 1707182 A1 | 10/2006 |
| EP | 1707183 A1 | 10/2006 |
| EP | 1773906 A1 | 4/2007 |
| EP | 1800671 A1 | 6/2007 |
| EP | 1903065 A2 | 3/2008 |
| EP | 2209472 A1 | 7/2010 |
| EP | 2271304 A1 | 1/2011 |
| EP | 2391424 A2 | 12/2011 |
| EP | 2591772 A1 | 5/2013 |
| EP | 2611466 A2 | 7/2013 |
| EP | 2726067 A1 | 5/2014 |
| EP | 2858630 A1 | 4/2015 |
| EP | 2859794 A1 | 4/2015 |
| EP | 2867298 A1 | 5/2015 |
| EP | 2925296 A1 | 10/2015 |
| EP | 2995217 A1 | 3/2016 |
| EP | 3020454 A1 | 5/2016 |
| FR | 2801209 A1 | 5/2001 |
| FR | 2815350 A1 | 4/2002 |
| FR | 2816834 A1 | 5/2002 |
| FR | 2835529 A1 | 8/2003 |
| FR | 2892931 A1 | 5/2007 |
| FR | 2902655 A1 | 12/2007 |
| FR | 2940093 A1 | 6/2010 |
| FR | 2957347 A1 | 9/2011 |
| FR | 2967062 A1 | 5/2012 |
| JP | H06362 A | 1/1994 |
| JP | H1080973 A | 3/1998 |
| JP | 2002-020451 A | 1/2002 |
| JP | 2003-081742 A | 3/2003 |
| JP | 2004-203917 A | 7/2004 |
| JP | 2004-256694 A | 9/2004 |
| JP | 2006-290845 A | 10/2006 |
| JP | 2009-292854 A | 12/2009 |
| JP | 2010-132568 A | 6/2010 |
| JP | 2010-163389 A | 7/2010 |
| JP | 2011-173851 A | 9/2011 |
| JP | 2011-246352 A | 12/2011 |
| JP | 2012-057110 A | 3/2012 |
| JP | 2013-502494 A | 1/2013 |
| JP | 2016-094362 A | 5/2016 |
| KR | 20080064230 A | 7/2008 |
| KR | 20090058294 A | 6/2009 |
| KR | 20090081582 A | 7/2009 |
| KR | 20110062277 A | 6/2011 |
| KR | 20140078356 A | 6/2014 |
| KR | 20140093349 A | 7/2014 |
| KR | 20140121154 A | 10/2014 |
| WO | 1989/007959 A1 | 9/1989 |
| WO | 1991/001970 A2 | 2/1991 |
| WO | 1994/13354 A1 | 6/1994 |
| WO | 1998/13025 A1 | 4/1998 |
| WO | 1998/26751 A1 | 6/1998 |
| WO | 1998/26756 A1 | 6/1998 |
| WO | 1999/12519 A1 | 3/1999 |
| WO | 1999/55288 A1 | 11/1999 |
| WO | 1999/55290 A1 | 11/1999 |
| WO | 1999/55291 A1 | 11/1999 |
| WO | 1999/55292 A1 | 11/1999 |
| WO | 1999/56708 A1 | 11/1999 |
| WO | 2000/14091 A1 | 3/2000 |
| WO | 2000/016752 A2 | 3/2000 |
| WO | 2000/018367 A1 | 4/2000 |
| WO | 2000/027350 A1 | 5/2000 |
| WO | 2000/40628 A1 | 7/2000 |
| WO | 2001/003652 A2 | 1/2001 |
| WO | 2001/024768 A2 | 4/2001 |
| WO | 2001/068037 A2 | 9/2001 |
| WO | 2001/078691 A1 | 10/2001 |
| WO | 2001/087065 A1 | 11/2001 |
| WO | 2001/094438 A1 | 12/2001 |
| WO | 2002/007699 A1 | 1/2002 |
| WO | 2002/039961 A1 | 5/2002 |
| WO | 2002/039964 A1 | 5/2002 |
| WO | 2002/043490 A1 | 6/2002 |
| WO | 2002/043491 A1 | 6/2002 |
| WO | 2002/045663 A1 | 6/2002 |
| WO | 2002/047620 A2 | 6/2002 |
| WO | 2002/047624 A1 | 6/2002 |
| WO | 2002/047626 A1 | 6/2002 |
| WO | 2002/047628 A1 | 6/2002 |
| WO | 2002/047657 A2 | 6/2002 |
| WO | 2002/047658 A2 | 6/2002 |
| WO | 2002/054997 A1 | 7/2002 |
| WO | 2002/055034 A2 | 7/2002 |
| WO | 2002/072045 A2 | 9/2002 |
| WO | 2003/028678 A1 | 4/2003 |
| WO | 2003/094870 A1 | 11/2003 |
| WO | 2004/110401 A2 | 12/2004 |
| WO | 2005/014777 A2 | 2/2005 |
| WO | 2005/017134 A2 | 2/2005 |
| WO | 2005/092963 A1 | 10/2005 |
| WO | 2006/015718 A1 | 2/2006 |
| WO | 2006/062740 A2 | 6/2006 |
| WO | 2006/127883 A2 | 11/2006 |
| WO | 2006/131403 A1 | 12/2006 |
| WO | 2007/057059 A1 | 5/2007 |
| WO | 2007/070643 A2 | 6/2007 |
| WO | 2007/071886 A2 | 6/2007 |
| WO | 2007/077029 A1 | 7/2007 |
| WO | 2007/145395 A1 | 12/2007 |
| WO | 2008/006677 A1 | 1/2008 |
| WO | 2008/006687 A1 | 1/2008 |
| WO | 2008/024408 A2 | 2/2008 |
| WO | 2008/125406 A2 | 10/2008 |
| WO | 2008/133982 A2 | 11/2008 |
| WO | 2008/148809 A1 | 12/2008 |
| WO | 2009/014347 A2 | 1/2009 |
| WO | 2009/053594 A2 | 4/2009 |
| WO | 2010/003138 A1 | 1/2010 |
| WO | 2010/006442 A1 | 1/2010 |
| WO | 2010/037402 A1 | 4/2010 |
| WO | 2010/076483 A1 | 7/2010 |
| WO | 2010/079468 A2 | 7/2010 |
| WO | 2010/086754 A2 | 8/2010 |
| WO | 2010/129299 A2 | 11/2010 |
| WO | 2011/016140 A1 | 2/2011 |
| WO | 2011/016531 A1 | 2/2011 |
| WO | 2011/022582 A1 | 2/2011 |
| WO | 2011/075556 A1 | 6/2011 |
| WO | 2011/089709 A1 | 7/2011 |
| WO | 2011/126978 A1 | 10/2011 |
| WO | 2011/140330 A2 | 11/2011 |
| WO | 2012/037445 A2 | 3/2012 |
| WO | 2012/063947 A1 | 5/2012 |
| WO | 2012/087510 A1 | 6/2012 |
| WO | 2012/105096 A1 | 8/2012 |
| WO | 2012/117013 A1 | 9/2012 |
| WO | 2012/121704 A1 | 9/2012 |
| WO | 2012/168102 A2 | 12/2012 |
| WO | 2013/064596 A1 | 5/2013 |
| WO | 2013/068478 A1 | 5/2013 |
| WO | 2013/071079 A1 | 5/2013 |
| WO | 2013/149323 A1 | 10/2013 |
| WO | 2013/165424 A1 | 11/2013 |
| WO | 2014/001574 A1 | 1/2014 |
| WO | 2014/001985 A1 | 1/2014 |
| WO | 2014/014139 A1 | 1/2014 |
| WO | 2014/105676 A1 | 7/2014 |
| WO | 2014/111579 A2 | 7/2014 |
| WO | 2014/176515 A2 | 10/2014 |
| WO | 2014/210117 A1 | 12/2014 |
| WO | 2015/020060 A1 | 2/2015 |
| WO | 2015/028417 A1 | 3/2015 |
| WO | 2015/028418 A1 | 3/2015 |
| WO | 2015/028421 A1 | 3/2015 |
| WO | 2015/028424 A1 | 3/2015 |
| WO | 2015/051139 A1 | 4/2015 |
| WO | 2015/188335 A1 | 12/2015 |
| WO | 2016/016315 A1 | 2/2016 |

(56) References Cited

FOREIGN PATENT DOCUMENTS

| WO | 2016/058958 A1 | 4/2016 |
|---|---|---|
| WO | 2016/069396 A2 | 5/2016 |
| WO | 2016/074683 A1 | 5/2016 |
| WO | 2016/087948 A2 | 6/2016 |
| WO | 2016/096928 A1 | 6/2016 |
| WO | 2016/100885 A1 | 6/2016 |
| WO | 2016/115257 A2 | 7/2016 |
| WO | 2016/138249 A1 | 9/2016 |
| WO | WO-2017112521 A1 * | 6/2017 |
| WO | 2017/155906 A1 | 9/2017 |
| WO | 2019/210121 A1 | 10/2019 |

OTHER PUBLICATIONS

Rahman, Synthesis and properties of waterborne polyurethane adhesives: effect of chain extender of ethylene diamine, butfanediol, and fluoro-butanediol. Journal of Adhesion Science and Technology. 2013;27(23):2592-2602.

U.S. Appl. No. 15/451,897, filed Mar. 7, 2017, U.S. Pat. No. 11,622,929, Issued.

U.S. Appl. No. 18/114,425, filed Feb. 27, 2023, Pending.

U.S. Appl. No. 17/530,662, filed Nov. 19, 2021, Abandoned.

U.S. Appl. No. 17/855,239, filed Jun. 30, 2022, Abandoned.

U.S. Appl. No. 18/168,215, filed Feb. 13, 2023, Pending.

Ma et al., Synthetic Leather Chemistry and Technology, 1st Edition. 4 pages, Nov. 30, 2015.

Chinese Office Action for Application No. 201980028764.2, dated Dec. 6, 2022, 17 pages.

Xu et al., Synthesis and Characterization of Cationic Waterborne Polyurethane based Polycarbonate Polyol. China Leather. Nov. 2011;40(21):1-14.

Yao et al., Application of bionic technology in textiles. Textile Dyeing and Finishing Journal. Dec. 2013;35(12):29-33.

Zhang et al., Working Manual of Large Scale Poultry Farm Laboratory. Golden Shield Publishing House. p. 138, Oct. 2013.

Chinese Office Action for Application No. 201880058933.2, dated Aug. 4, 2021, 26 pages.

U.S. Appl. No. 16/348,644, filed May 9, 2019, 2019-0359786, Published.

U.S. Appl. No. 16/128,620, filed Sep. 12, 2018, 2019-0076347, Published.

U.S. Appl. No. 17/071,198, filed Oct. 15, 2020, Pending.

Adina, Natpure Hollowbead. Adina Cosmetic Ingredients Ltd., retrieved online at: http://www.cosmeticingredients.co.uk/ingredient/natpure-hollowbead. 2 pages, (2015).

AkzoNobel, Product Specification for Expancel Microspheres. www.expancel.com, 2 pages, (2011).

Araujo et al., Techniques for reducing residual monomer content in polymers: a review. Polymer Engineering and Science. 64 pages, Jul. 1, 2002.

Lochhead et al., Polymers in Cosmetics: Recent Advances. From film-formers to rheology modifiers, polymers serve various functions. Retrieved online at: https://www.happi.com/contents/view_features/2005-11-15/polymers-in-cosmetics-recent-advances. 12 pages, Nov. 15, 2005.

Srivastava et al., Indian Application No. 148/DEL/2010. Bioreactor and Uses Thereof. Filed Jul. 29, 2011. 20 pages.

Teixeira et al., A case study of product engineering: Performance of microencapsulated perfumes on textile applications. AIChE Journal. Jun. 2011;58(6):1939-1950.

U.S. Appl. No. 17/231,587, filed Apr. 15, 2021, Pending.

U.S. Appl. No. 17/326,605, filed May 21, 2021, Pending.

* cited by examiner

Initial

After 75%RH for 15 min

Initial

After
75%RH
for 15 min

LONG LASTING COSMETIC COMPOSITIONS

RELATED APPLICATIONS

This application is a § 371 national stage filing of PCT/US2019/029274, filed Apr. 26, 2019, which claims priority to U.S. Provisional Application No. 62/663,315, filed Apr. 27, 2018, the entire contents of each of which are incorporated herein by reference.

BACKGROUND

Polyurethanes and polyurethane-ureas are a well-known class of synthetic polymers with broad utility in multiple industries. This versatility is derived from the ability to prepare polyurethanes from a large and diverse set of potential monomers. These diverse monomer options allow the realization of an equally diverse set of physical properties. Hence, the resulting polyurethanes can be in many different forms including e.g., soft foams, elastomers, adhesive films, or hard plastics, and can be used in many different types of products including bedding, foot wear, adhesives, and automobile parts.

Among these many forms of polyurethanes, waterborne polyurethanes (WBPUs) and polyurethane-ureas (WBPU-Us) have been used as film forming agents in commercially available personal care products. When used as hair fixatives, these film forming polymers provide style-holding benefits. The problem with the use of WBPUs and WBPU-Us for consumer-based cosmetic products has been the lack of performance and overall consistency in application. For example, common polyurethane products such as Luviset® P.U.R, DynamX, and DynamX $H_2O$ lack elasticity. This leads to an undesirable stiff feeling when applied to hair. Avalure UR 405, Baycusan C1004, Baycusan C1008, and Polyderm PE/PA ED, however, are very flexible (i.e., do not lack elasticity). Yet, these products have poor initial curl hold and elicit a gummy feeling. Other problems associated with the use of WBPUs and WBPU-Us include, but are not limited to, flaking upon touching or combing (e.g., dusty micro-flakes shown on hair fibers); undesirable tactile feelings upon touch (e.g., brittle, stiff, or tacky, gummy); poor humidity resistance (e.g., styling resins absorb moisture and weigh down hair resulting in a loss of style); lack of movement (e.g., plastic-like mold shape; hair curls don't move with motion; can't easily comb through; gummy; lack of bounciness); and short-lived hair styles (e.g., hair styles, curls, waves, etc. don't last long—on average styles typically last less than a half day).

Previously, we identified a combination of selection markers that could be used to determine whether certain WBPU based cosmetic compositions, such as hair fixatives, would result in improved performance. See WO 2017/155906 the entire contents of which are incorporated herein by reference. In one aspect, e.g., we have shown that compositions comprising WBPUs having a Young's modulus above 150 MPa, an elongation at break from about 15% to about 300%, and a moisture uptake of less than 10%, provide long-lasting and natural hairstyles. See WO 2017/155906. Here, we focus on improving the mechanical properties while maintaining a moisture uptake of less than 10%, which was previously demonstrated to be optimal for achieving long-lasting styling performance.

SUMMARY

It has now been found that the long-lasting characteristics arising from WBPUs possessing our previously disclosed combination of mechanical properties can by further enhanced by incorporating at least one multi-functional chain extender (such as a triol or tetraol) into the composition. Provided herein, therefore, are hair treatment compositions comprising a polyurethane-urea crosslinked by at least one multi-functional chain extender such as a hydrocarbon based triol or tetraol, wherein the Young's modulus of the polyurethane-urea is above 150 MPa; the elongation at break of the polyurethane-urea is from about 15% to about 300%; and the moisture uptake of the polyurethane-urea is less than 10%. In one aspect, the use of these multi-functional chain extenders provided hair compositions with better hold and stronger humidity resistance over those previously described. See e.g., FIG. 1, which shows a comparison of the in vivo performance of PU 419, an inventive WBPU crosslinked by multi-functional chain extender, with a commercial resin. As shown, PU 419 displays better initial hold and stronger humidity resistance.

It has also been found that incorporating nanoparticles into WBPU-based compositions possessing the proper combination of mechanical properties described above further improve the long-lasting effects of WBPUs in hair treatment products. Thus, in another aspect, also provided herein are hair treatment compositions comprising a polyurethane-urea and at least one nanoparticle, wherein the Young's modulus of the polyurethane-urea is above 150 MPa; the elongation at break of the polyurethane-urea is from about 15% to about 300%; and the moisture uptake of the polyurethane-urea is less than 10%. These compositions were found to outperform commercial resins in both initial curl hold and curl retention after high humidity stress. See e.g., FIG. 2, which shows a comparison of the in vitro performance of PU 427, an inventive WBPU/silica nanocomposite synthesized by in situ polymerization, with a commercial resin and comparator PU 339. As shown, PU 427 displays better initial hold and stronger humidity resistance. In addition, FIG. 4 shows the in vitro curl retention under 75% relative humidity for 15 minutes of PU 339 following post-blend with 1% Aerosil 200 (silica nanoparticles) or 0.25% $TiO_2$. As shown, PU 339 post-blend with nanoparticles showed better initial curl hold and curl retention after high humidity. Taken together, this data shows that the disclosed nanocomposite technology applies generally to compositions comprising a polyurethane-urea having the disclosed mechanical properties, and is not limited to only those which comprise a multi-functional chain extender.

DETAILED DESCRIPTION

1. Definitions

Figure 1:
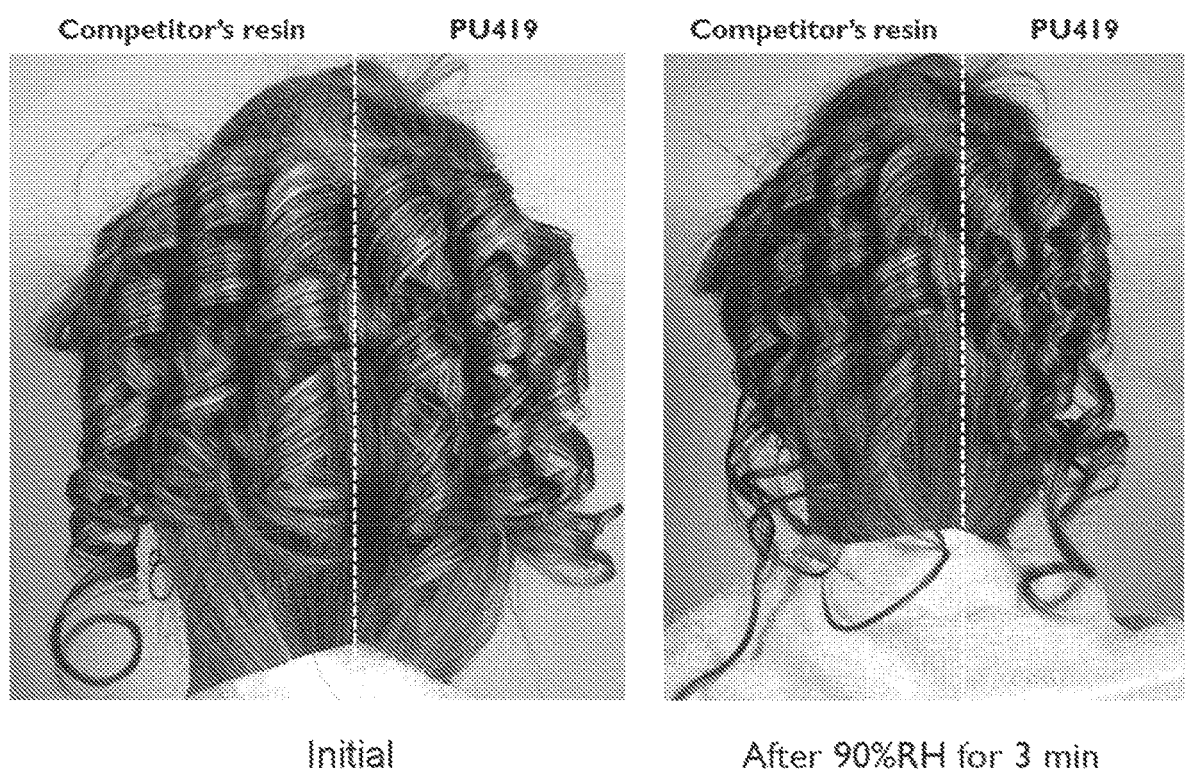
FIG. 1 shows the in vivo performance of a WBPU crosslinked by multi-functional chain extender of the present disclosure (PU 419) compared to a commercial resin.

As used herein, "cationic polyurethanes" refer to thermoplastic polymers comprising carbamate (urethane) groups and which bear an overall net positive charge at pH≤7. "Cationic polyurethane-ureas" refer to thermoplastic polymers comprising a —O—C(O)—NR— and a —NR—C(O)—NR-linkage and which bear an overall net positive charge at pH≤7. In some aspects, the cationic polyurethanes and cationic polyurethane-ureas described herein bear an overall net positive charge at pH from about 3.7 to about 6.5, from about 3.7 to about 6.0, or from about 3.7 to about 5.5. Unless otherwise specified, cationic polyurethanes and cationic polyurethane-ureas, when used herein, include amphoteric/cationic polyurethanes and polyurethane-ureas. In one aspect, however, cationic polyurethanes and cationic polyurethane-ureas do not encompass amphoteric/cationic polyurethanes or amphoteric/cationic polyurethane-ureas.

As used herein, "amphoteric polyurethanes" refer to thermoplastic polymers comprising carbamate (urethane) groups and which can act both as a cationic or an anionic polyurethanes depending on neutralization method. "Amphoteric polyurethane-ureas" refer to thermoplastic polymers comprising a —O—C(O)—NR— and a —NR—C(O)—NR-linkage and which can act both as a cationic or an anionic polyurethanes depending on neutralization method. An "amphoteric/cationic polyurethane" or "amphoteric/cationic polyurethane-urea" means that the described amphoteric species is one which acts as a cationic polyurethane or cationic polyurethane-urea when neutralized with an acid. An "amphoteric/anionic polyurethane" or "amphoteric/anionic polyurethane-urea" means that the described amphoteric species is one which acts as an anionic polyurethane or anionic polyurethane-urea when neutralized with a base.

As used herein, "anionic polyurethanes" refer to thermoplastic polymers comprising carbamate (urethane) groups and which bear an overall net negative charge at pH≥7. "Anionic polyurethane-ureas" refer to thermoplastic polymers comprising a —O—C(O)—NR— and a —NR—C(O)—NR-linkage and which bear an overall net negative charge at pH≥7. Unless otherwise specified, anionic polyurethanes and anionic polyurethane-ureas, when used herein, include amphoteric/anionic polyurethanes and amphoteric/anionic polyurethane-ureas. In one aspect, however, anionic polyurethanes and anionic polyurethane-ureas do not encompass amphoteric/anionic polyurethanes or amphoteric/anionic polyurethane-ureas.

"Young's modulus (or the modulus of elasticity, tensile modulus)" is a measure of the stiffness of a solid polymer film. Young's modulus, E, can be calculated by dividing the tensile stress by the extensional strain in the elastic (initial, linear) portion of the stress-strain curve. The Young's modulus of the waterborne polyurethanes and waterborne polyurethane-ureas can be determined by a protocol defined to measure mechanical properties, and is developed in reference to ASTM D638, ASTM D412, test guidelines as described below in Example 1.

The "elongation at break (also known as fracture strain, ultimate elongation)" is the ratio between changed length and initial length after breakage of the solid polymer film. The elongation at break of the waterborne polyurethanes and waterborne polyurethane-ureas can be determined by a protocol defined to measure mechanical properties, and is developed in reference to ASTM D638, ASTM D412, test guidelines as described below in Example 1.

The "moisture uptake" is the measure of water adsorbed by the solid polymer film. The method for determining the moisture uptake of the solid polymer film is provided in Example 2.

A "sensory score" may be determined by the performance of the hair fixative. In one aspect, the tress with the composition applied is blow dried for 90 seconds. The tresses are prepared in duplicate and blinded randomly and evaluated for natural feeling and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes.

The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

2. Selection Markers

Provided herein are specific combinations of WBPU-U properties that have been found to result in cosmetic compositions (e.g., hair products) having substantially improved performance. Those properties include e.g., a combination of certain mechanical properties, a combination of certain chemical properties, or a combination of both mechanical and chemical properties.

Young's Modulus, Elongation at Break, and Moisture Uptake

The combination of mechanical properties described herein include the Young's modulus (e.g., above 150 MPa), the elongation at break (e.g., from about 15% to about 300%), and hydrophobicity (moisture uptake, e.g., less than 10%).

In one aspect, the Young's modulus of the polyurethane-urea described herein should be above about 150 MPa. For example, the Young's modulus of the polyurethane-urea in the disclosed compositions may be above about 160 MPa, above about 170 MPa, above about 180 MPa, above about 190 MPa, above about 200 MPa, above about 210 MPa, above about 220 MPa, above about 230 MPa, above about 240 MPa, above about 250 MPa, above about 260 MPa, above about 270 MPa, above about 280 MPa, above about 290 MPa, above about 300 MPa, above about 310 MPa, above about 320 MPa, above about 330 MPa, above about 340 MPa, above about 350 MPa, above about 360 MPa, above about 370 MPa, above about 380 MPa, above about 390 MPa, above about 400 MPa, above about 410 MPa, above about 420 MPa, above about 430 MPa, above about 440 MPa, above about 450 MPa, above about 460 MPa, above about 470 MPa, above about 480 MPa, above about 490 MPa, above about 500 MPa, above about 510 MPa, above about 520 MPa, above about 530 MPa, above about 540 MPa, or above 550 MPa. In other aspects, the Young's modulus of the polyurethane-urea should be between about 150 MPa and about 500 MPa. For example, the Young's modulus of the polyurethane-urea in the disclosed compositions may be between about 150 MPa and about 400 MPa, between about 150 MPa and about 350 MPa, between about 170 MPa and about 390 MPa, between about 180 MPa and about 320 MPa, between about 190 MPa and about 300

MPa, between about 200 MPa and about 290 MPa, or between about 210 MPa and about 280 MPa.

In one aspect, the elongation at break of the polyurethane-urea in the disclosed compositions should be from about 15% to about 300%. For example, the elongation at break of the polyurethane-urea in the disclosed compositions may be from about 20% to about 300%, from about 25% to about 300%, from about 40% to about 280%, from about 100% to about 280%, from about 100% to about 250%, from about 150% to about 250%, from about 200% to about 250%, from about 210% to about 250%, about 30% to about 150%, from about 15% to about 150%, from about 150% to about 300%, from about 50% to about 250%; from about 75% to about 225%, or from about 100% to about 200%. The elongation break may be optionally combined with one or more of the Young's modulus values described in the paragraph above or any one of the Young's modulus values described in the remainder of the disclosure.

In one aspect, the moisture uptake of the polyurethane-urea in the disclosed compositions should be less than about 10%. For example, the moisture uptake of the polyurethane-urea in the disclosed compositions may be less than about 9.5%, less than about 9%, less than about 8.5%, less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, less than about 0.5%, or is about 0%. In one aspect, the moisture uptake of the polyurethane-urea in the disclosed compositions should be from about 0% to about 10%. For example, the moisture uptake may be from about 0% to about 8%, from about 2% to about 8%, or from about 3% to about 7%. The moisture uptake may be optionally combined with one or more of the Young's modulus values, one or more of the elongation break values, or both as described in the paragraphs above or in the remainder of the disclosure.

As shown in the Exemplification section below, polyurethane-ureas having the Young's modulus, elongation at break, and moisture uptake described above improve initial hold and display better curl retention under high humidity.

3. Compositions

In a first embodiment, provided herein are hair fixative compositions comprising a polyurethane-urea crosslinked by at least one hydrocarbon based triol or tetraol, wherein the Young's modulus of the polyurethane-urea is above 150 MPa; the elongation at break of the polyurethane-urea is from about 15% to about 300%; and the moisture uptake of the polyurethane-urea is less than 10%.

In a second embodiment, the polyurethane-urea described in the composition of the first embodiment is anionic.

In a third embodiment, the polyurethane-urea described in the composition of the first or second embodiment is a salt of the formula: [Q, W, V, Y and Z]X, wherein
Q is the product formed from polyisocyanate;
W is the product formed from polycarbonate polyol monomer;
V is the product formed from hydrocarbon based triol or tetraol;
Y is the product formed from $C_3$-$C_8$alkyldiol optionally substituted with —(O)OH or a mono-amino$C_3$-$C_8$alkyldiol;
Z is the product formed from $C_3$-$C_8$alkyldiamine optionally substituted with —(O)OH; and
X is a neutralizer.

In a fourth embodiment, the polyisocyanate described in the composition of the third embodiment is selected from tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, 1,5-diisocyanato naphthalene, 4,4'-methylenebis(cyclohexyl isocyanate) ($H_{12}$MDI) and norbornene diisocyanate, wherein the remaining features are as described above in the first or second embodiment. In one alternative, the polyisocyanate described in the composition of the third embodiment is isophorone diisocyanate, wherein the remaining features are as described above in the first or second embodiment.

In a fifth embodiment, the polycarbonate polyol monomer described in the composition of the third embodiment has a molecular weight ranging from about 500 g/mol to about 4,000 g/mol, wherein the remaining features are as described above in the first, second, third, or fourth embodiment. Alternatively, the polycarbonate polyol monomer described in the composition of the third embodiment has a molecular weight ranging from about 750 g/mol to about 3,500 g/mol, wherein the remaining features are as described above in the first, second, third, or fourth embodiment. In another alternative, the polycarbonate polyol monomer described in the composition of the third embodiment has a molecular weight ranging from about 1,000 g/mol to about 3,000 g/mol, wherein the remaining features are as described above in the first, second, third, or fourth embodiment. In yet another alternative, the polycarbonate polyol monomer described in the composition of the third embodiment has a molecular weight of about 1,000 g/mol or about 2,000 g/mol or about 3,000 g/mol, wherein the remaining features are as described above in the first, second, third, or fourth embodiment.

In a sixth embodiment, Y in the composition of the third embodiment is the product formed from $C_3$-$C_8$alkyldiol optionally substituted with —(O)OH, wherein the remaining features are as described above in the first, second, third, fourth, or fifth embodiment. Alternatively, Y in the composition of the third embodiment is the product formed from 2,2-bis(hydroxymethyl)butyric acid, wherein the remaining features are as described above in the first, second, third, fourth, or fifth embodiment.

In a seventh embodiment, Z in the composition of the third embodiment is lysine, wherein the remaining features are as described above in the first, second, third, fourth, fifth, or sixth embodiment.

In an eighth embodiment, the neutralizer in the composition of the third embodiment is $Na_2CO_3$, triethylamine, or lactic acid, wherein the remaining features are as described above in the first, second, third, fourth, fifth, sixth, or seventh embodiment. Alternatively, the neutralizer in the composition of the third, fourth, fifth, sixth, or seventh embodiment is $Na_2CO_3$, wherein the remaining features are as described above in the first, second, third, fourth, fifth, sixth, or seventh embodiment.

In a ninth embodiment, V in the composition of the third embodiment is glycerol, trimethylol propane, erythritol, or pentaerythritol, wherein the remaining features are as described above in the first, second, third, fourth, fifth, sixth, seventh, or eighth embodiment. Alternatively, V in the composition of the third, fourth, fifth, sixth, or seventh embodiment is glycerol or erythritol, wherein the remaining features are as described above in the first, second, third, fourth, fifth, sixth, seventh, or eighth embodiment.

In a tenth embodiment, the molar ratio of W to Q in the composition of the third embodiment is about 0.2:1 to about 0.3:1, wherein the remaining features are as described above in the first, second, third, fourth, fifth, sixth, seventh, eighth, or ninth embodiment. Alternatively, the molar ratio of W to Q in the composition of the third embodiment is about 0.22:1 to about 0.3:1, wherein the remaining features are as described above in the first, second, third, fourth, fifth, sixth, seventh, eighth, or ninth embodiment.

In an eleventh embodiment, the molar ratio of V to Q in the composition of the third embodiment is about 0.10:1 to about 0.26:1, wherein the remaining features are as described above in the first, second, third, fourth, fifth, sixth, seventh, eighth, ninth, or tenth embodiment. Alternatively, the molar ratio of V to Q in the composition of the third embodiment is about 0.12:1 to about 0.24:1, wherein the remaining features are as described above in the first, second, third, fourth, fifth, sixth, seventh, eighth, ninth, or tenth embodiment.

In a twelfth embodiment, the molar ratio of Y to Q in the composition of the third embodiment is about 0.18:1 to about 0.25:1, wherein the remaining features are as described above in the first, second, third, fourth, fifth, sixth, seventh, eighth, ninth, tenth, or eleventh embodiment. Alternatively, the molar ratio of Y to Q in the composition of the third embodiment is about 0.20:1 to about 0.23:1, wherein the remaining features are as described above in the first, second, third, fourth, fifth, sixth, seventh, eighth, ninth, tenth, or eleventh embodiment.

In a thirteenth embodiment, the molar ratio of Z to Q in the composition of the third embodiment is about 0.05:1 to about 0.40:1, wherein the remaining features are as described above in the first, second, third, fourth, fifth, sixth, seventh, eighth, ninth, tenth, eleventh, or twelfth embodiment. Alternatively, the molar ratio of Z to Q is about 0.11:1 to about 0.34:1, wherein the remaining features are as described above in the first, second, third, fourth, fifth, sixth, seventh, eighth, ninth, tenth, eleventh, or twelfth embodiment.

In a fourteenth embodiment, the polyurethane-urea of the first or second embodiment is of the Formula I or II:

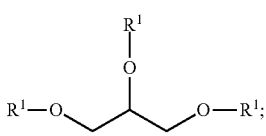
(I)

or

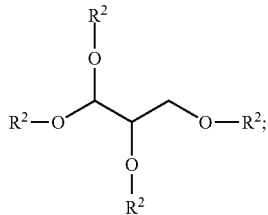
(II)

or a salt thereof, wherein each $R^1$ and $R^2$ are independently repeating units of the formula:

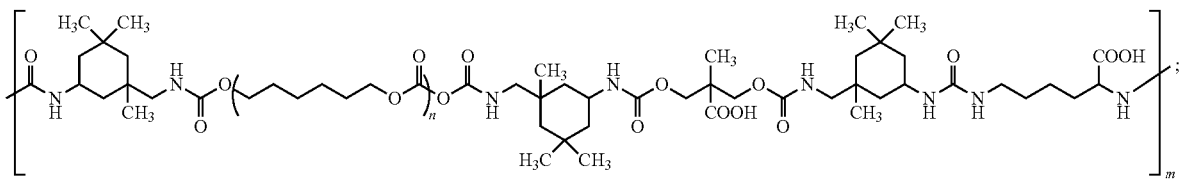

wherein n is from 6 to 21 and m is from 5 to 15.

In a fifteenth embodiment, the polyurethane-urea of the first or second embodiment is selected from any one of those described in the Exemplification section below. Both neutral and salt forms of the polyurethane-ureas are included.

In a sixteenth embodiment, the polyurethane-urea of the first embodiment is cationic.

In a seventeenth embodiment, the polyurethane-urea of the first and sixteenth embodiment is of the formula: [Q', W', V', Y' and Z']X', wherein
  Q' is the product formed from polyisocyanate;
  W' is the product formed from polycarbonate polyol monomer;
  V' is the product formed from hydrocarbon based triol or tetraol;
  Y' is the product formed from $C_1$-$C_8$alkyldiol monomer;
  Z' is the product formed from $C_{1-8}$aminoalkyldiol monomer; and
  X' is a neutralizer.

In an eighteenth embodiment, the polyisocyanate in the composition of the sixteenth embodiment is isophorone diisocyanate monomer, wherein the remaining features are as described in the first or fifteenth embodiment.

In an nineteenth embodiment, Y' in the composition of the sixteenth embodiment is the product formed from 1,4-butanediol monomer, wherein the remaining features are as described in the first, fifteenth, or eighteenth embodiment.

In a twentieth embodiment, Z' in the composition of the sixteenth embodiment is the product formed from 3-(dimethylamino)-1,2-propanediol monomer, wherein the remaining features are as described in the first, fifteenth, eighteenth, or nineteenth embodiment.

In a twenty-first embodiment, the compositions described in any one of the first to twentieth embodiment, further comprise nanoparticles.

In a twenty-second embodiment, the compositions described in any one of the first to twenty-first embodiment, further comprise nanoparticles, wherein the nanoparticles are incorporated into the polyurethane-urea (e.g., through in situ polymerization).

In a twenty-third embodiment, the compositions described in any one of the first to twenty-second embodiment, further comprise nanoparticles, wherein the nanoparticles are post-blended with the composition.

In a twenty-fourth embodiment, the nanoparticles described in any one of the twentieth to twenty-third embodiments are fumed silica or titanium dioxide nanoparticles.

In a twenty-fifth embodiment, also provided herein is a hair treatment composition comprising a polyurethane-urea and at least one nanoparticle, wherein the Young's modulus of the polyurethane-urea is above 150 MPa; the elongation at break of the polyurethane-urea is from about 15% to about 300%; and the moisture uptake of the polyurethane-urea is less than 10%. In one aspect, the at least one nanoparticle of this embodiment is incorporated into the polyurethane-urea (e.g., through in situ polymerization). Alternatively, the at least one nanoparticle of this embodiment is post-blended with the composition. The nanoparticle described in this embodiment may be fumed silica or titanium dioxide nanoparticle.

In a twenty-sixth embodiment, the polyurethane-urea of the twenty-fifth embodiment is selected from any one of those described in the Exemplification section below. Both neutral and salt forms of the polyurethane-ureas are included.

The compositions described herein may further comprise oils. Oils for use in the disclosed compositions can be selected from mineral, animal, plant or synthetic oils. In one aspect, the oil is linoleic acid or a mixture of fatty acids. Examples include, but are not limited to fragrance oils, emollients, monoterpenoids, fatty alcohols, fatty acids, fatty esters, fatty ethers, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyl-tetralin), and mixtures thereof. In another aspect, the oil is present in an amount ranging from about 0.2 to about 1.65% based on the total weight of the composition. In another aspect, the oil is present in an amount of about 0.2 to about 0.25% based on the total weight of the composition.

In one aspect, the disclosed compositions are applied to the hair with water.

In one aspect, the disclosed compositions, when applied to the hair, change the texture and appearance.

In one aspect, the disclosed compositions, when applied to the hair, improve hold, i.e., hair that is formed into a given curl or style retains that curl or style over time.

In one aspect, the disclosed compositions, when applied to the hair, provide sufficient stylability, i.e., the composition applied to hair supplies sufficient rigidity and flexibility to form and maintain a style.

In one aspect, the disclosed compositions, when applied to the hair, minimize flyaways, i.e., there are minimal individual hair fibers that do not conform to the given curl or style.

In one aspect, the disclosed compositions, when applied to the hair, preserves curl shape, i.e., hair that is formed into a given curl retains that curl over time.

In one aspect, the disclosed compositions, when applied to the hair, provides natural curl enhancement, i.e., hair that naturally tends to curl displays a more defined and less diffused curl pattern.

The compositions described herein may further comprise an antioxidant. Antioxidants that may be suitable with the compositions described herein include, but are not limited to, açai oil, alpha lipoic acid, green and white tea, retinol, vitamin C, Vitamin E, butylated hydroxytoluene, butylated hydroxyanisole, coenzyme Q10 (Co Q-10), isoflavones, polyphenols, curcumin, turmeric, pomegranate, rosemary, glutathione, selenium, and zinc.

4. Methods of Use

The compositions described herein may be used for any cosmetic application. Such applications include, but are not limited to, skin-care creams, eye and facial makeup (e.g., mascara, eye liner, eyebrow makeup, and the like), deodorants, lotions, powders, perfumes, baby products, body butters; and hair products (e.g., permanent chemicals, hair colors, hair sprays, and gels).

In one aspect, the compositions described herein are used as a hair product, e.g., in a conventional manner for providing hairstyle/hold benefits.

In an exemplary aspect, an effective amount of a composition described herein may be sprayed or applied onto dry or damp hair before and/or after the hair is styled. As used herein "effective amount" means an amount sufficient to provide the hair hold and style performance desired according to the length and texture of the hair.

In one aspect, the present disclosure provides a method of fixing hair comprising the step of applying a polyurethane disclosed herein. In one aspect, the present disclosure provides a method of retaining the curl of hair comprising the step of applying polyurethane disclosed herein.

In one aspect, the present disclosure also includes a method to determine the curl retention of a hair tress. In one aspect, the method of measuring the curl retention of a hair tress includes the steps of a) measuring the length of the hair tress; b) applying a composition disclosed herein to the hair tress; c) blow drying the hair tress without brushing; d) curling the hair tress with a heated curling rod; e) mechanically manipulating the hair tress by pulling, combing and brushing; and f) measuring the length of the curled hair tress.

In one aspect, the method of measuring the curl retention of a hair tress, includes the steps of a) measuring the length of the hair tress; b) applying a composition described herein to the hair tress; c) blow drying the hair tress without brushing; d) curling the hair tress heated curling rod; e) subjecting the hair tress to humidity; and f) measuring the length of the curled hair tress. In one aspect, the curled hair tress is subjected to 60%, 70%, 75%, 80% or 90% relative humidity for 3, 5, 10, 15, 20, 25, 30, 35, 40, 45, 50, 55, 60, 75, 90, 105, 120, 180 or 210 minutes at a temperature of 25° C.

EXEMPLIFICATION

Example 1. Methods for Determining Mechanical Performance

The Young's modulus is a measure of the ability of a material to withstand changes in length when under uniaxial tension or compression. A higher Young's modulus typically indicates that the material is more rigid. The elongation at break, also known as fracture strain, is the ratio between changed length and initial length after breakage of the test specimen. A higher elongation at break expresses the capability of a material to resist fracture. For a composition applied to hair to hold the shape of the hair, the Young's modulus and elongation at break of the composition should be such that the composition provides rigidity to the hair but is not brittle.

A comparison of Young's modulus and the elongation at break for the some of the polyurethanes disclosed herein was made to several commercially available polyurethane products. The Young's modulus and the elongation at break can be determined by a protocol defined to measure mechanical properties is developed in compliance with ASTM D638, ASTM D412, test guidelines. In particular, the following protocol can be used to determine the Young's modulus and elongation at break (or ultimate elongation) of dry film of polyurethanes. Testing requires approximately 10-20 min per sample to complete.

Materials:
>25 g polyurethane aqueous dispersion
1 clean rectangular mold (2 mm×20 mm×45 mm) grooved on Teflon sheet per sample
1 clean razor blade
Scotch tape
Universal Testing Machine mounted with extension grip geometry Sample Preparation:
1. Prepare 25 g of 10 wt % WBPU solution from their respective stock solution.
2. Apply 2.5 mL prepared solution in each mold (2 mm×20 mm×45 mm) and allow drying for 2 days to give WBPU film.
3. After it dries out, use a spatula to remove film from the mold.
4. Use the razor blade to cut corners and get film with around 15 mm width and around 150-300 micron thickness. Make sure that the film is free of air bubbles.
5. Label the test film.
6. Cut four pieces of tape (20 mm) per sample and adhere them to both sides of the specimen strip and make a dog-bone shaped sample to improve hold of sample in grip. Store the prepared test films in desiccators for 1-2 hour to fully dry them. Take one sample out of desiccators at a time for testing.

Sample Testing
1. Balance the load registering on the universal testing machine so that it reads 0 Newtons.
2. Use calipers to set a distance of 20 mm between the top and bottom extension grip geometries.
3. Mount a sample in the extension grips and secure tightly, ensuring that the scotch tape is not visible, and that the sample is as close to vertical as possible in both vertical planes.
4. Stretch the sample slightly, by separating the geometries until a force of 25 N is registered.
5. Begin a tensile testing run on the universal testing machine at a speed of 100 mm/minute, stopping the test upon sample fracture.
6. Elongation at break is calculated at the elongation at which the material fractures.
7. Young's modulus is calculated as the modulus during the initial, elastic portion of deformation by calculating the slope of a linear fit to that region with an R value >0.99.
  a) low modulus and high elongation (Avalure UR 450, C1004, Polyderm PE/PA ED, Polyderm PE/PA), which leads to inferior curl hold (e.g., hold is temporary, transient, or short-lived) or
  b) high modulus and low elongation (DynamX, DynamX/ $H_2O$, Luviset PUR), which leads to a brittle material with low performance (e.g., resin is brittle or fractures) after manipulation.

Example 2. Methods for Determining Hydrophobicity/Water Uptake

The moisture uptake properties, under highly humid environment, of WBPU dry films have been linked to their long lasting hold performance. As such, it is important to be able to reproducibly and accurately evaluate such moisture uptake properties to enable predictive in vitro and in vivo evaluation of WBPU dry films. The following protocol can be used to determine moisture uptake ability of WBPU dry films under high humid environment. Test requires about 2-3 days per sample set to complete Materials
>15 g WBPU solution
1 clean cell culture petri dish (60 mm dia×15 mm H) per sample
Humidity chamber with flexibility to control temperature and relative humidity (RH)

Sample Testing
1. Prepare 15 g of 10 wt % WBPU solution from their respective stock solution.
2. Label cell culture petri dishes for each sample and measure their empty weight ($W_{pd}$).
3. Apply 4 mL prepared solution in each petri dish (3 samples per WBPU and allow to equilibrate for 20 hours at 25° C. and 50% RH in humidity chamber.
4. After equilibration, measure and record sample weight ($W_i$).
5. Place the samples to humidity chamber at 25° C. and 90% RH and allow equilibration to high humidity for 20 hours.
6. Measure and record final sample weight ($W_f$).

Sample Analysis
Calculate % moisture uptake using the following equation:

$$\% \text{ moisture uptake} = \left[\frac{((Wf - Wpd) - (Wi - Wpd))}{(Wi - Wpd)}\right] \times 100\%$$

Example 3. Compositions and Properties of WBPU-Us Having Chain Extenders or Nanoparticles Through In Situ Polymerization Compositions comprising a polyurethane-urea crosslinked by at least one hydrocarbon based triol or tetraol were formulated by water or mixture of water and ethanol. The ratio of the constituents in the final blend is listed in Table 1

TABLE 1

| PU Name | NCO | Polyol (molar ratio to NCO) | Alcohols chain extender (molar ratio to NCO) | Ionic chain extender (molar ratio to NCO) | Non-ionic chain extender (molar ratio to NCO) | Weight percent of fumed silica | Neut. | Degree of Neut. | Oil |
|---|---|---|---|---|---|---|---|---|---|
| 419 | IPDI | PCD1K (0.30) | Glycerol (0.18) | DMBA (0.23) | LL (0.20) | NP | $Na_2CO_3$ | 100% | NP |
| 420 | IPDI | PCD1K (0.30) | Erythritol (0.14) | DMBA (0.23) | LL (0.20) | NP | $Na_2CO_3$ | 100% | NP |

TABLE 1-continued

| PU Name | NCO | Polyol (molar ratio to NCO) | Alcohols chain extender (molar ratio to NCO) | Ionic chain extender (molar ratio to NCO) | Non-ionic chain extender (molar ratio to NCO) | Weight percent of fumed silica | Neut. | Degree of Neut. | Oil |
|---|---|---|---|---|---|---|---|---|---|
| 424 | IPDI | PCD1K (0.22) | Erythritol (0.12) | DMBA (0.20) | LL (0.34) | NP | Na$_2$CO$_3$ | 100% | NP |
| 425 | IPDI | PCD1K (0.22) | Erythritol (0.24) | DMBA (0.20) | LL (0.11) | NP | Na$_2$CO$_3$ | 100% | NP |
| 426 | IPDI | PCD1K (0.26) | Erythritol (0.13) | DMBA (0.21) | LL (0.27) | NP | Na$_2$CO$_3$ | 100% | NP |
| 427 | IPDI | PCD1K (0.31) | BD (0.27) | DMBA (0.23) | LL (0.19) | 1% | Na$_2$CO$_3$ | 100% | Mixture of FAs |
| 428 | IPDI | PCD1K (0.30) | BD (0.27) | DMBA (0.23) | LL (0.19) | 5% | Na$_2$CO$_3$ | 100% | Mixture of FAs |

IPDI = isophorone diisocyanate; PCD1K = polycarbonate diol with molecular weight at 1,000 g/mol; BD = 1,4-butanediol; DMBA = 2,2-bis(hydroxymethyl)butyric acid; LL = L-lysine; and FA = fatty acids.
NP = not present Of the compositions listed in Table 1, PU 420, 424, 425, 426, and 428 have an elongation at break lower than 15%, are therefore considered to be compositions with suboptimal mechanical properties. Those having mechanical properties within the disclosed ranges are shown in Table 2.

TABLE 2

| PU Name | Young's Modulus (MPa) | Elongation at break (%) | Water Uptake (%) |
|---|---|---|---|
| *339 (Comparator 1) | 388 ± 23 | 14 ± 5 | 5.6 ± 0.44 |
| 419 | 407 ± 77 | 12 ± 4 | 5.62 ± 1.05 |
| 427 | 349 ± 28 | 20 ± 9 | 8.73 ± 0.39 |

*PU 339 comprises polycarbonate polyol, IPDI, DMBA, 1,4-BD, LL, and fatty acid, i.e., No hydrocarbon based triol or tetraol was used.

Figure 2:
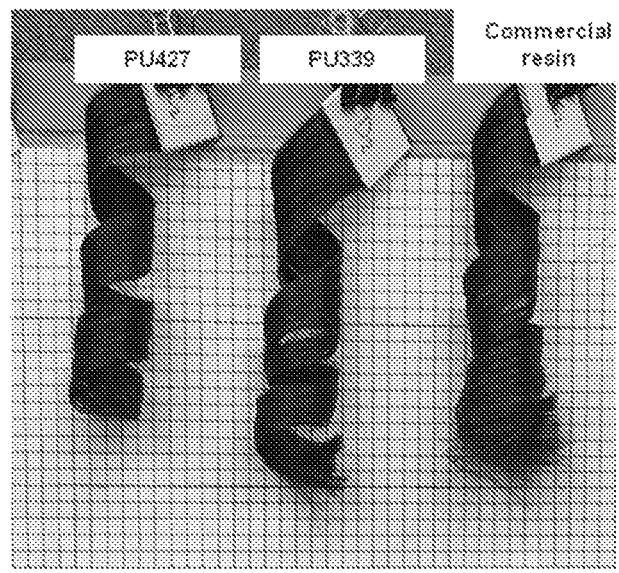
FIG. 2 shows the in vitro performance of a WBPU/silica nanocomposite of the present disclosure synthesized by in situ polymerization (PU 427) compared to a commercial resin and comparator PU 339.
Figure 2:
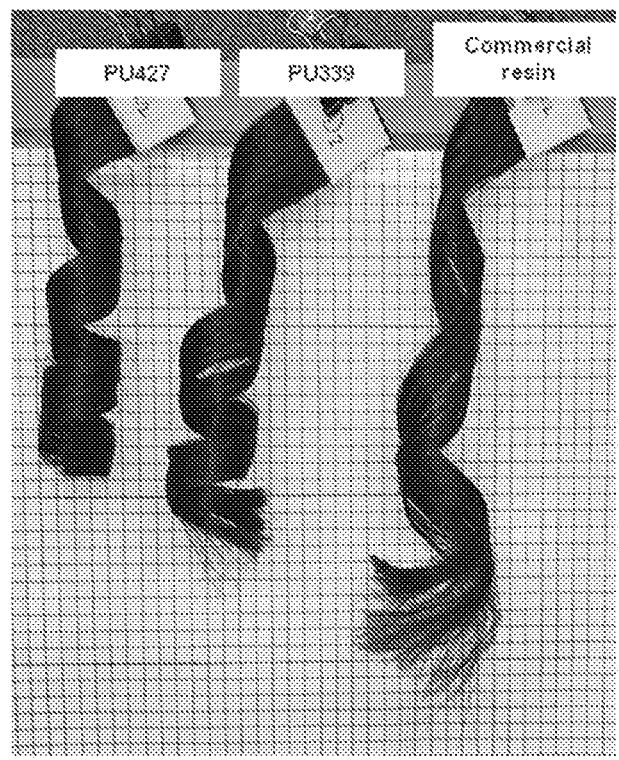
Figure 3:
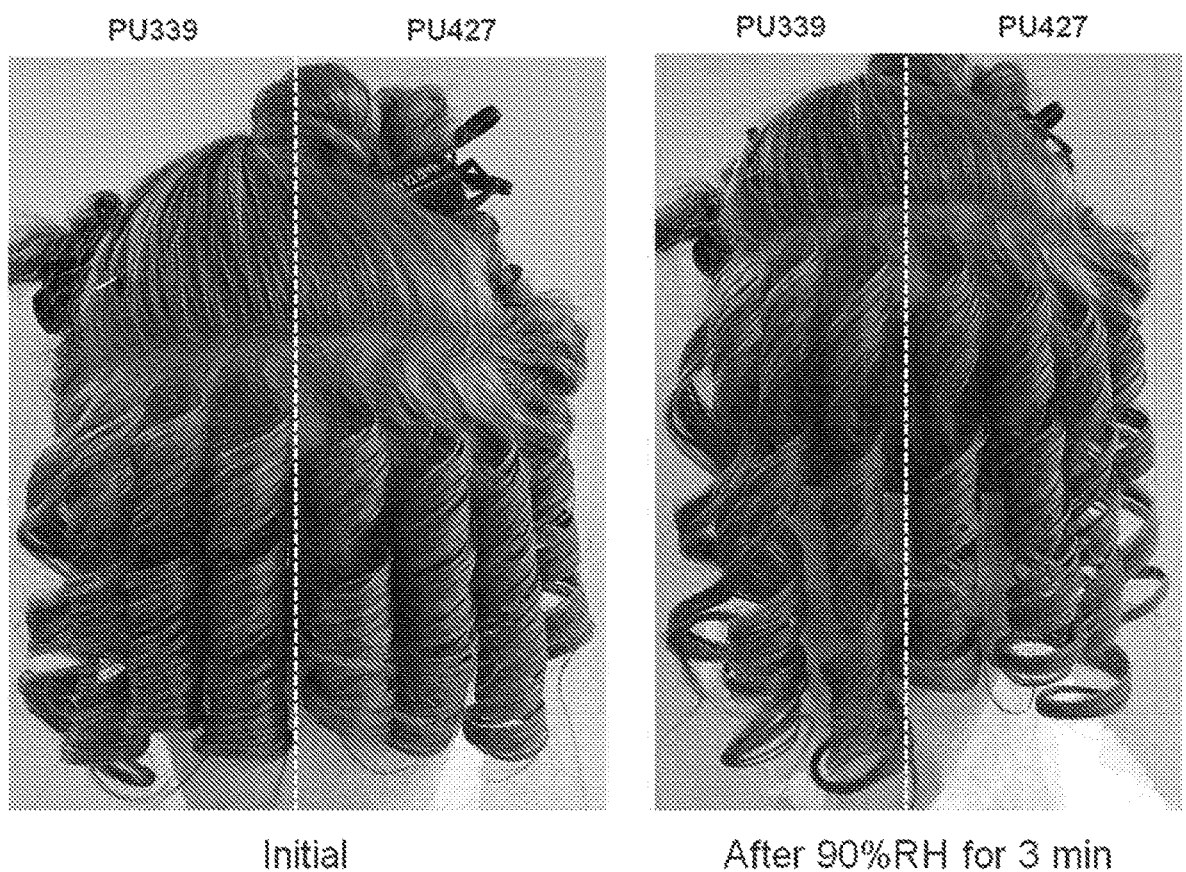
FIG. 3 shows the in vivo performance between PU 427 and comparator PU 339.

FIG. 2 shows the in vitro performance of the WBPU/silica nanocomposite PU 427 compared to a commercial resin and comparator PU 339. As shown, PU 427 showed better initial hold as well as stronger humidity resistance. In an in vivo mannequin head test, PU 427 also demonstrated better curl retention than PU 339 under 90% humidity for 3 min. See FIG. 3.

Example 4. Nanoparticle Post-Blending Incorporation

The incorporation of nanoparticles to WBPU compositions having the disclosed properties was investigated. Fumed silica and titanium dioxide (TiO$_2$) were explored. As shown in Table 3, when fumed silica nanoparticles, Aerosil 200 and Aerosil 300 (Evonik) were incorporated through post-blending, PU 339 showed improved mechanical properties. With increasing fumed silica concentration from 1% to 10% (with respect to waterborne polyurethane solid content), Young's modulus increased significantly; elongation at break, on the other hand, remained similar as that for PU 339. All WBPU/fumed silica nanocomposites showed low water uptake, i.e., 5.4-6.9%.

TABLE 3

| WBPU | Fumed Silica | Loading conc. | Young's modulus (MPa) | Elongation at break (%) | Water uptake (%) |
|---|---|---|---|---|---|
| PU 339 | — | — | 388 ± 23 | 14 ± 5 | 5.6 ± 0.44 |
| | Aerosil 200 | 1% | 436 ± 3 | 11 ± 3 | 6.9 ± 0.35 |
| | | 5% | 499 ± 23 | 14 ± 4 | 6.69 ± 0.27 |
| | | 10% | 508 ± 13 | 10 ± 4 | N/A |
| | Aerosil 300 | 1% | 393 ± 14 | 8 ± 5 | 5.79 ± 0.26 |
| | | 5% | 451 ± 13 | 12 ± 3 | 5.39 ± 0.09 |
| | | 10% | 535 ± 24 | 10 ± 3 | N/A |

Figure 4:
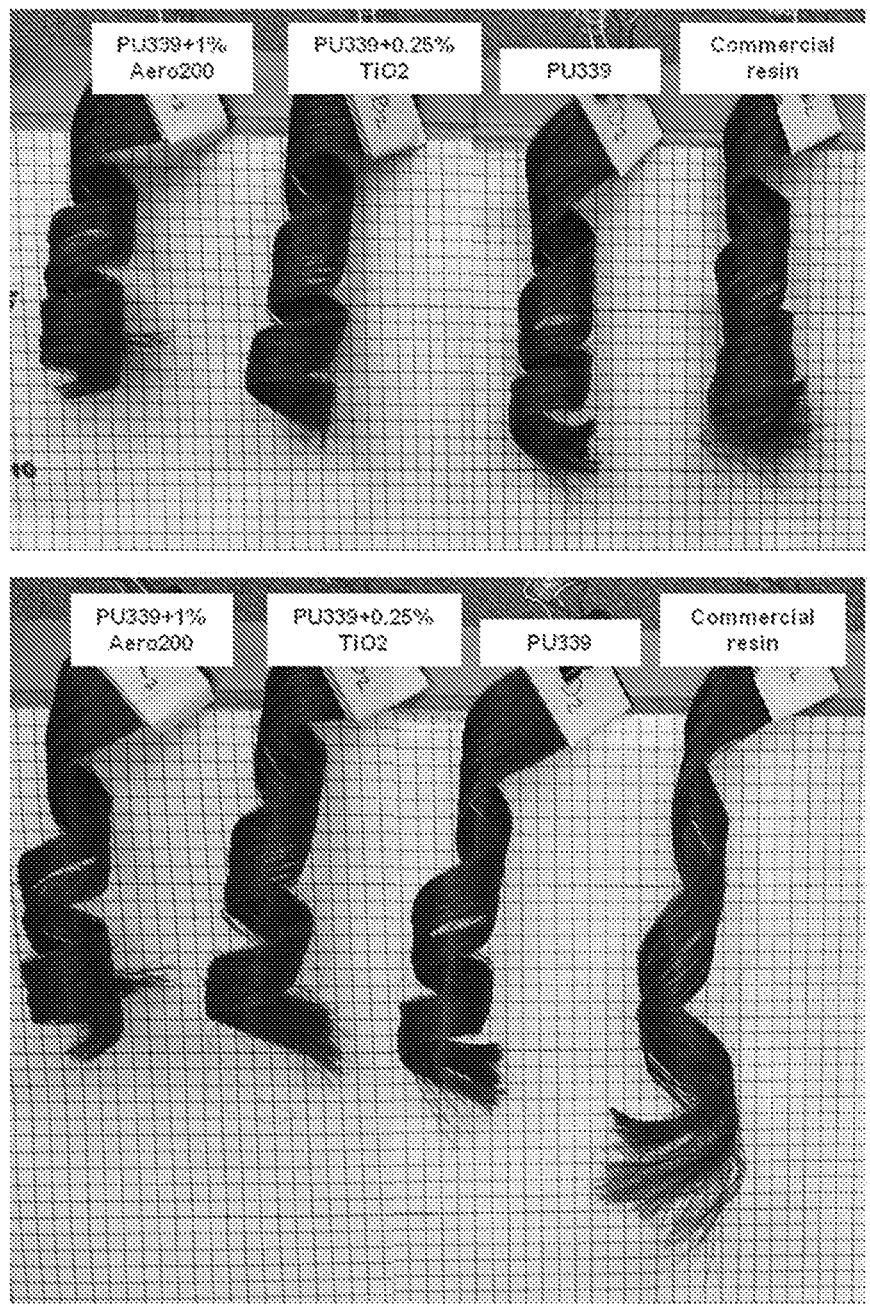
FIG. 4 shows the in vitro curl retention under 75% relative humidity for 15 minutes of comparator PU 339 following post-blend with 1% Aerosil 200 (silica nanoparticles) or 0.25% $TiO_2$.

Titanium dioxide (TiO$_2$) nanoparticles were also incorporated into PU 339 through post-blending. In Table 4, the results show a significant increase of Young's modulus when 0.25% (with respect to waterborne polyurethane solid content) of TiO$_2$ was post-blended into WBPU, similar to the WBPU/fumed silica systems (Table 3). Conversely, increasing loading concentration of TiO$_2$ from 0.25% to 0.5% or 1% did not further enhance mechanical properties of WBPU. In vitro testing shows that, when 1% Aerosil 200 or 0.25% TiO$_2$ was post-blended in PU 339, both initial curl hold and curl retention after high humidity stress were improved; moreover, the post-blended WBPU nanocomposites as well as PU 339 all performed much better than commercial resin (FIG. 4). All WBPU/TiO$_2$ nanocomposites showed low water uptake, i.e., around 6.7%.

TABLE 4

| WBPU | Nanoparticles | Loading conc. | Young's modulus (MPa) | Elongation at break (%) | Water uptake (%) |
|---|---|---|---|---|---|
| PU 339 | — | — | 388 ± 23 | 14 ± 5 | 5.6 ± 0.44 |
| | TiO$_2$ | 0.25% | 500 ± 23 | 15 ± 5 | 6.7 ± 0.33 |
| | | 0.5% | 503 ± 32 | 23 ± 12 | N/A |
| | | 1% | 510 ± 26 | 12 ± 8 | 6.7 ± 0.15 |

As previously described, compositions comprising WBPUs having a Young's modulus above 150 MPa, an elongation at break from about 15% to about 300%, and a moisture uptake of less than 10%, provide long-lasting and natural hairstyles. The above data establishes that crosslinking these WBPUs with at least one hydrocarbon based triol or tetraol leads to hair compositions with better hold and stronger humidity resistance. The above data also establishes that incorporating nanoparticles into WBPU-based compositions possessing the proper combination of mechanical properties further enhance the long-lasting characteristic of WBPUs in hair treatment products.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A hair treatment composition comprising a polyurethane-urea crosslinked by at least one hydrocarbon based triol or tetraol, wherein the polyurethane-urea is a salt of the formula: [Q, W, V, Y and Z]X, wherein
   Q is the product formed from polyisocyanate;
   W is the product formed from polycarbonate polyol monomer;
   V is the product formed from hydrocarbon based triol or tetraol;
   Y is the product formed from $C_3$-$C_8$alkyldiol optionally substituted with —C(O)OH or a mono-amino$C_3$-$C_8$alkyldiol;
   Z is the product formed from $C_3$-$C_8$alkyldiamine optionally substituted with —C(O)OH; and
   X is a neutralizer;
and wherein the Young's modulus of the polyurethane-urea is above 150 MPa; the elongation at break of the polyurethane-urea is from about 15% to about 300%; and the moisture uptake of the polyurethane-urea is less than 10%.

2. The composition of claim 1, wherein the polyurethane-urea is anionic.

3. The composition of claim 1, wherein the polyisocyanate is selected from tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, 1,5-diisocyanato naphthalene, 4,4'-methylenebis(cyclohexyl isocyanate) ($H_{12}$MDI) and norbornene diisocyanate.

4. The composition of claim 1, wherein the polycarbonate polyol monomer has a molecular weight ranging from about 500 g/mol to about 4,000 g/mol.

5. The composition of claim 1, wherein Y is the product formed from $C_3$-$C_8$alkyldiol optionally substituted with —(O)OH.

6. The composition of claim 1, wherein Z is lysine.

7. The composition of claim 1, wherein the neutralizer is $Na_2CO_3$, triethylamine, or lactic acid.

8. The composition of claim 1, wherein V is glycerol, trimethylol propane, erythritol, or pentaerythritol.

9. The composition of claim 1, wherein the molar ratio of W to Q is about 0.2:1 to about 0.3:1.

10. The composition of claim 1, wherein the molar ratio of V to Q is about 0.10:1 to about 0.26:1.

11. The composition of claim 1, wherein the molar ratio of Y to Q is about 0.18:1 to about 0.25:1.

12. The composition of claim 1, wherein the molar ratio of Z to Q is about 0.05:1 to about 0.40:1.

13. The composition of claim 1, wherein the polyurethane-urea is of the Formula I or II:

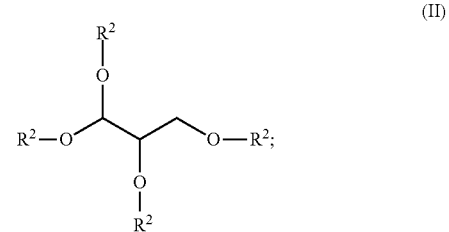

or a salt thereof, wherein each $R^1$ and $R^2$ are independently repeating units of the formula:

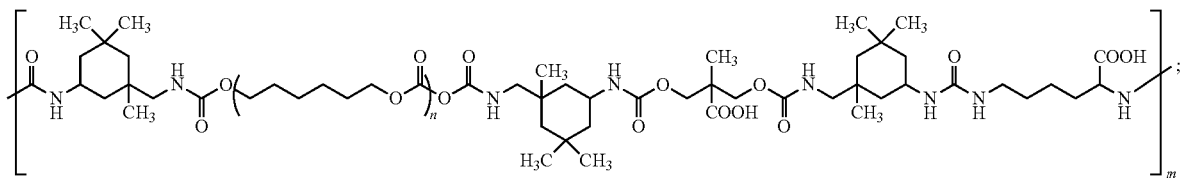

wherein n is from 6 to 21 and m is from 5 to 15.

14. The composition of claim 1, wherein the composition further comprises nanoparticles.

15. A method of preserving curl in human hair, said method comprising administering to the hair a composition according to claim 1.

* * * * *